United States Patent [19]
Bahrmann et al.

[11] Patent Number: 6,051,743
[45] Date of Patent: Apr. 18, 2000

[54] PROCESS FOR THE PREPARATION OF PREDOMINANTLY UNBRANCHED HIGHER PRIMARY ALCOHOLS

[75] Inventors: Helmut Bahrmann, Hamminkeln; Gregor Deckers, Xanten; Wolfgang Greb, Dinslaken; Peter Heymanns, Essen; Peter Lappe; Thomas Müller, both of Dinslaken; Jürgen Szameitat, Wesel; Ernst Wiebus, Oberhausen, all of Germany

[73] Assignee: Hoechst Aktiengesellschaft, Germany

[21] Appl. No.: 08/163,086

[22] Filed: Dec. 7, 1993

[30] Foreign Application Priority Data

Dec. 17, 1992 [DE] Germany ............... 42 42 725

[51] Int. Cl.⁷ ............... C07C 29/14; C07C 29/143; C07C 29/16; C07C 45/00
[52] U.S. Cl. ............... 568/882; 568/454
[58] Field of Search ............... 568/882, 454

[56] References Cited

U.S. PATENT DOCUMENTS

| | | | |
|---|---|---|---|
| 2,560,360 | 7/1951 | Mertzweiller et al. | 568/882 |
| 2,755,308 | 7/1956 | Rottig et al. | 568/882 |
| 4,578,523 | 3/1986 | Bahrmann et al. | 568/454 |
| 4,593,126 | 6/1986 | Cornils et al. | 568/454 |
| 4,795,727 | 1/1989 | Bach et al. | 568/454 |
| 4,801,754 | 1/1989 | Bach et al. | 568/454 |
| 4,808,757 | 2/1989 | Cornils et al. | 568/454 |
| 4,808,758 | 2/1989 | Bach et al. | 568/454 |
| 5,200,380 | 4/1993 | Herrmann et al. | 568/454 |

FOREIGN PATENT DOCUMENTS

| | | |
|---|---|---|
| 16 32 34 | 12/1985 | European Pat. Off. |
| 30 237 5 | 2/1989 | European Pat. Off. |

OTHER PUBLICATIONS

Database WPI, Week 8931, Derwent Publications; AN–89–224459 JPA–1–160, 928; Jun. 23, 1989.

*Primary Examiner*—Alan L. Rotman
*Attorney, Agent, or Firm*—Bierman, Muserlian and Lucas

[57] ABSTRACT

For the preparation of predominantly unbranched higher primary alcohols, olefins from the Fischer-Tropsch synthesis are reacted with hydrogen and carbon monoxide in the presence of water and a catalyst which is rhodium, in metallic form or as a compound, and a water-soluble phosphine. The reaction product obtained is hydrogenated. The water-soluble phosphines employed are compounds whose anion is a phosphine containing at least one sulfonated or carboxylated aromatic radical and whose cation is a quaternary ammonium or phosphonium ion.

11 Claims, No Drawings

PROCESS FOR THE PREPARATION OF PREDOMINANTLY UNBRANCHED HIGHER PRIMARY ALCOHOLS

This Application claims the benefit of the priority of German Application P 42 42 725.8, filed Dec. 17, 1992.

The invention relates to a process for the preparation of predominantly unbranched higher primary alcohols by hydroformylation of olefins resulting from the Fischer-Tropsch synthesis in the presence of water-soluble rhodium complex compounds as catalysts.

BACKGROUND OF THE INVENTION

Higher unbranched primary alcohols, i.e. those containing 6 to 20 carbon atoms, are extensively used as intermediates in the chemical industry. For instance, $C_8$- to $C_{12}$-alcohols are esterified with phthalic acid to produce plasticizers distinguished by good low-temperature flexibility. Sodium salts of n-alkyl sulfates, which are obtained by esterification of concentrated sulfuric acid with unbranched fatty alcohols, are biologically degradable and consequently have acquired great importance as environmentally compatible synthetic detergents. Esters based on straight-chain primary alcohols and branched dicarboxylic acids are valuable lubricants which are used, in particular, in aircraft engines.

The examples of uses for straight-chain primary alcohols given above explain the great interest in processes for their preparation which start from inexpensive raw materials and which can be carried out with great technical simplicity. A further requirement is that the straight-chain feedstocks not isomerize in the course of preparation and that, where it is possible for secondary and/or tertiary alcohols to form along with the desired primary alcohols, clear preference is given to the latter.

In accordance with DE-C-2 855 421, $C_9$-alcohols are prepared by dimerization of butenes in the presence of organoaluminum compounds as catalysts to give an octene mixture; thereafter, the mixture is hydroformylated. The resultant $C_9$-alcohols are reacted with phthalic acid to form dinonylphthalate plasticizers.

By hydroformylation of a butene fraction, aldol condensation of the resulting aldehyde mixture, and subsequent hydrogenation, $C_{10}$-alcohols are obtained which are processed further by the process described in EP-A 366 089 to give esters of phthalic acid.

Another route to obtain didecyl phthalate mixtures is described in EP-A-424 767. The esters are prepared in a multistage process by dimerization of butene mixtures, hydroformylation and hydrogenation of the resulting octene mixture to give a nonanol mixture, and dehydration of the nonanol mixture to form a mixture of nonenes. This mixture is hydroformylated and hydrogenated to form a decanol mixture, which is then esterified to produce the desired product.

The known methods still fail to meet all of the economic and technical demands made on a process carried out on the industrial scale. For instance, the starting materials are not always available in sufficient quantity or at favorable cost, or their conversion to the desired straight-chain alcohols requires complex processes.

SUMMARY OF THE INVENTION

Therefore, the object was to develop a process which starts from inexpensive raw materials and which produces a high yield of the desired alcohols by a simple route. This object is attained by the present invention which consists of a process for the preparation of predominantly unbranched higher primary alcohols by reacting olefins with carbon monoxide and hydrogen to give aldehydes. The reaction takes place in the liquid phase at temperatures of 20° to 150° C. and pressures of 0.1 to 20 MPa in the presence of water and a rhodium catalyst. The catalyst is in metallic form or as a compound, and further contains a water-soluble phosphine. The aldehydes are hydrogenated to give the corresponding alcohols.

The process comprises reacting olefins obtained by the Fischer-Tropsch synthesis and having from 6 to 20 carbon atoms in the molecule, or mixtures of such olefins, in the presence of water-soluble salts. The anion of such salts is a phosphine containing at least one sulfonated or carboxylated aromatic radical and the cation or cations, which correspond in number to the charge on the anion, are one or more of the formula

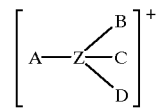

wherein Z is nitrogen or phosphorus, A is alkyl having 7 to 18 carbon atoms or aralkyl having 7 to 18 carbon atoms, and B, C and D are straight or branched chain alkyl having 1 to 4 carbon atoms.

DETAILED DESCRIPTION OF THE INVENTION

The olefins used as starting materials in accordance with the process claimed are obtained by the Fischer-Tropsch synthesis. This term refers to the hydrogenation of carbon monoxide in the presence of solid catalysts, which proceeds with the construction of aliphatic molecular chains. Catalysts which have proven effective are the metals such as iron, cobalt, nickel, and ruthenium, with iron having acquired particular importance in practice.

The technical implementation of the synthesis (cf. in this respect e.g. Ullmanns Encyclopädie der technischen Chemie (Ullmann's Encyclopedia of Industrial Chemistry, 4th Edition (1977), volume 14, pages 329 ff.) involves the development of a series of different processes, of which two are currently in industrial use. In the "Arge process", hydrogen and carbon monoxide are reacted in fixed-bed reactors at a pressure of 2.5 MPa and at temperatures of 220° to 225° C. The "synthol process" operates with entrained-bed reactors at 2.3 MPa and 320 to 340° C.

Irrespective of the process used, the Fischer-Tropsch synthesis is not very selective, but yields complex mixtures which contain saturated and unsaturated hydrocarbons of different molecular size, as well as alcohols, aldehydes, ketones, and acids. The proportion of olefins in the reaction product may be as much as approximately 70%, with the predominant compounds being unbranched and having from 5 to 18 carbon atoms in the molecule and a terminal double bond. The components of the reaction mixture are separated from one another in a conventional manner by distillation. The latter may be followed by a fine purification to obtain individual compounds in high purity. For example, branched hydrocarbons may be separated from their straight-chain isomers via urea inclusion compounds.

The hydroformylation of the olefins obtained as described above must be carried out under conditions which ensure that straight-chain aldehydes are formed. Consequently, the carbonyl group must be directed to the terminal carbon atom of the olefin molecule and, in addition, the double bond must retain its position in the molecule under the reaction conditions, i.e. it may not move from the terminal position to a position within the molecular chain. As a solution to this problem, it has proven particularly suitable to react the unsaturated compounds with carbon monoxide and hydrogen in a liquid two-phase system which comprises, as the organic phase, the olefin (which may be dissolved in an organic solvent) and the reaction product which is being formed. The aqueous phase is the catalyst solution containing the rhodium compound and a water-soluble phosphine.

The water-soluble phosphines employed are salts whose anion is formed from a phosphine which contains at least one sulfonated or carboxylated aromatic radical; the term phosphine also includes those compounds of trivalent phosphorus in which the phosphorus atom is a component of a heterocyclic ring. The aromatic radical can be attached directly or via other groups to the phosphorus atom of the phosphine. Examples of aromatic radicals are phenyl and the naphthyl, which may be mono- or polysulfonated or -carboxylated and may, in addition, be substituted by other substituents, such as alkyl, hydroxyl, and halogen (especially fluorine). Apart from monophosphines, polyphosphines (especially diphosphines) which contain at least one sulfonated or carboxylated aromatic radical, can also form the anion. Examples of suitable monophosphines are triphenylphosphine mono-, di- or -trisulfonates or - carboxylates. Diphosphine anions are preferably derived from biaryl compounds of the formula

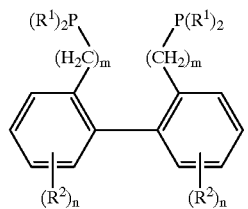

which are substituted by at least one sulfonate ($SO_3^-$) or carboxylate ($COO^-$). In the formula, the $R^1$'s are individually alkyl, cycloalkyl, phenyl, tolyl, or naphthyl; the $R^2$'s are individually hydrogen, alkyl having 1 to 14 carbon atoms, alkoxy having 1 to 14 carbon atoms, cycloalkyl, aryl, or aryloxy each having 6 to 14 carbon atoms, or a fused-on benzene ring. The m's are individually integers from 0 to 5, and the n's are individually integers from 0 to 4. Proven representatives of this class of compounds are the products obtained by sulfonation of 2,2'-bis(diphenylphosphineomethyl)-1,1'-biphenyl or 2,2'-bis(diphenylphosphinomethyl)-1,1'-binaphthyl. One example of the anion of a heterocyclic phosphorus compound which can be mentioned is 3,4-dimethyl-2,5,6-tris(p-sulfonatophenyl)-1-phosphanorbornadiene.

As a cation, the salts contain—depending on the charge on the anion—at least one ion of the formula

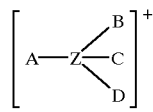

in which Z is nitrogen or phosphorus, A is alkyl having 7 to 18 carbon atoms or aralkyl having 7 to 18 carbon atoms, and B, C, and D are straight or branched chain alkyls having 1 to 4 carbon atoms.

Examples of cations of the structure mentioned which are suitable for carrying out the novel process are trimethylcetylammonium, trimethyldodecylammonium, tributyldodecylammonium, dodecylethyldimethylammonium, triethylbenzylammonium, trimethyltetradecylphosphonium, and tributylhexadecylphosphonium.

The onium compounds used as a component of the catalyst according to the novel process promote the solubility of the organic substrate in the aqueous phase and hence contribute to increasing the conversion. Their extremely low solubility in the organic phase means that they themselves—and the metal component of the catalyst system—are discharged from the reaction zone with the reaction product either not at all or only in negligible amounts. It is, therefore, unnecessary to include a separate step for recovery of rhodium from the aldehyde.

It is particularly important that, when using the water-soluble phosphines in the procedure claimed, the olefins employed in accordance with the invention are hydroformylated with high activity and selectivity, with the structure of the reacted hydrocarbons being maintained, i.e. at most, there is an insignificant amount of isomerization. In addition, the effect of the phosphines is such that terminal olefins are hydroformylated almost exclusively. The separation effect achieved thereby results in a further reduction in the proportion of the undesired branched compounds in the end product.

The preparation of the salts used in the process claimed is known. The starting materials are phosphines or phosphorus heterocycles containing sulfonated or carboxylated aryl radicals. The incorporation of the sulfonate radical is carried out by established methods, e.g. by treating the starting compounds with oleum. By varying the reaction conditions, in particular the reaction time and temperature, as well as the ratio of phosphorus compound to sulfur trioxide, the degree of sulfonation of the starting compounds can be controlled.

The carboxylated phosphorus compounds can be obtained by a variety of routes, for example by reacting the basic structures with carbonyl halides and, in particular, via Grignard compounds, by reaction with carbon dioxide.

Expediently, the compounds initially obtained from the reaction product are amine salts which are insoluble in water but soluble in organic solvents. They are subsequently converted by treatment with a quaternary ammonium or phosphonium hydroxide into the desired onium salt of the sulfonated or carboxylated triarylphosphine.

Reaction of the olefins with hydrogen and carbon monoxide according to the novel process is advantageously carried out at temperatures of 20° to 150° C., in particular 50° to 120° C., and at pressures of 0.1 to 20 MPa, in particular 1 to 10 MPa.

The catalyst added to the reaction system may be preformed. It can also, however, be prepared with equal success from the components—the rhodium or rhodium compound and the aqueous solution of the quaternary ammonium or phosphonium salt of the phosphine containing sulfonated or carboxylated aromatic radicals—under the reaction conditions in the reaction mixture, i.e. in the presence of the olefins. In addition to metallic rhodium in finely divided form, the rhodium source may comprise water-soluble rhodium salts such as rhodium chloride, rhodium sulfate, rhodium acetate, or compounds soluble in organic media, such as rhodium 2-ethylhexanoate, or insoluble compounds such as rhodium oxides.

The rhodium concentration in the aqueous catalyst solution is from 10 to 2000 ppm by weight, based on the solution. The quaternary ammonium or phosphonium salt of the sulfonated or carboxylated phosphine is employed in an amount such that from 1 to 1000 mol, preferably from 2 to 300 mol, of phosphine compound is present per mol of rhodium. The pH of the aqueous catalyst solution should not be less than 2. The solution is generally adjusted to a pH of from 2 to 13, preferably from 4 to 10.

The composition of the synthesis gas, i.e. the ratio of carbon monoxide to hydrogen, can be varied within broad limits. The synthesis gas generally employed is one in which the volume ratio of carbon monoxide to hydrogen is 1:1, or one which deviates only slightly from this value.

The reaction can be carried out either batchwise or continuously. The hydroformylation mixture is separated from the catalyst solution by simple phase separation. Hydrogenation can be carried out without further pretreatment. However, it is also possible to first separate the aldehydes from the accompanying by-products by distillation. The addition of hydrogen is carried out in known manner in the presence of the catalyst. Suitable examples are hydrogenation catalysts based on nickel, chromium, or copper. Conventionally, the hydrogenation temperature is between 100° and 180° C. and the pressure is between 1 and 10 MPa. For purification, the alcohols are distilled. They are especially suitable as the alcohol component of phthalic acid esters which are to be used as plasticizers, and for the production of alkylsulfonates and ester lubricants.

The following example illustrates the process according to the invention but does not limit it.

EXAMPLE

Experiment 1

Hydroformylation

A 1 liter autoclave is charged with 185 g of an olefin mixture from the Fischer-Tropsch synthesis containing predominantly n-nonenes and, as the catalyst, 550 g of an aqueous solution containing 66 mol % of trisodium tri(m-sulfophenyl)phosphine and 33 mol % of tri(trimethyltetradecyl)-ammonium Tri(m-sulfophenyl)phosphine, togehter with 5.44 ml of rhodium acetate solution (rhodium concentration: 20.21 g Rh/liters, corresponding to a content in the combined solutions of 80 mmol of P(III) and 200 ppm by weight of Rh and, to adjust the pH to about 6, 27.5 g of a buffer solution comprising 10 mol of Na acetate and 1 mol of glacial acetic acid per liter of solution.

The autoclave is flushed with nitrogen a number of times to remove oxygen. Synthesis gas (volume ration $CO/H_2$= 1:1) is then passed into the mixture at a pressure of 2.5 MPa and at 125° C. with stirring. The reaction is terminated after 6 hours, the pressure in the autoclave is released, and the organic phase (reaction product) is removed via a dip pipe and analyzed. The conversion of olefin is 85 % and remains unchanged on repeating the reaction ten times with the same catalyst solution.

Experiment 2

Hydrogenation

The crude product of Experiment 1 is hydrogenated in an autoclave with hydrogen in the presence of 2% by weight (based on the crude product) of a commercial nickel catalyst (60% by weight of Ni on kieselguhr) for 3 hours at 8 MPa and 150° C. When the reaction ends the reaction vessel is cooled, the pressure is released, and the product is separated from the catalyst.

Experiment 3

Purification of the Crude Alcohol

The crude alcohol from Experiment 2 is distilled in a 1 m column which is filled with 3 mm coils of stainless (VA) steel. An initial fraction is taken off at a head temperature of 93° C. and a pressure of 6.7 kPa, followed by an intermediate fraction at 145° C. and 6.7 kPa. The main fraction (26% by weight of the crude alcohol employed) is obtained at a head temperature of 147° C. and a pressure of 6.7 kPa. The alcohol contained in the crude product is 99.7%.

Experiment 4

Esterification of the Pure Alcohol 2.3 mol of the isodecanol from Experiment 3 is reacted with 1 mol of phthalic anhydride at 135° C. in the presence of 6 mmol of concentrated sulfuric acid, with the simultaneous removal of the water of reaction as an azeotrope with cyclohexane. When the reaction is complete, the sulfuric acid is neutralized with 5% sodium hydroxide solution, and the excess alcohol is separated by steam distillation at 135° and 1.5 kPa. The residue is dried with nitrogen at 135° C. and a pressure of 2 to 3 kPa and then filtered. The ester is obtained as a clear liquid.

In comparison to commercial ester plasticizers, whose viscosity (at 20° C.) is from 120 to 130 mPa.s, the plasticizer produced using the alcohol according to the invention is distinguished by its very low viscosity of 64.8 mPa.s (at 20° C.), which indicates the high degree of linearity of the alcohol used.

While only a limited number of specific embodiments of the present invention have been expressly disclosed, it is, nonetheless, to be broadly construed and not to be limited except by the character of the claims appended hereto.

What we claim is:

1. A process for the preparation of predominantly unbranched primary alcohols having 10 carbon atoms comprising reacting an olefin with carbon monoxide and hydrogen to form at least one aldehyde, said reaction taking place in a liquid phase at 20° to 150° C. and under a pressure of 0.1 to 20 MPa in the presence of water and a catalyst, said catalyst comprising metallic rhodium and/or a rhodium compound and a water-soluble phosphine, and hydrogenation of said aldehyde to at least one corresponding alcohol, said olefin having 9 carbon atoms being obtained from the Fischer-Tropsch synthesis containing also ketones and acids, in the presence of at least one water soluble salt comprising an anion having a charge thereon, and at least one cation, the number of which corresponds to said charge, said anion being a phosphine containing at least one sulfonated or carboxylated aromatic radical, said cation being of the formula

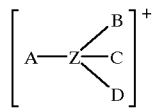

wherein Z is nitrogen or phosphorous, A is alkyl having 7 to 18 carbon atoms or aralkyl having 7 to 18 carbon atoms, and B, C, and D are individually straight or branched chain alkyl having 1 to 4 carbon atoms.

2. The process of claim 1 wherein said phosphine is a monophosphine.

3. The process of claim 1 wherein said phosphine is a diphosphine.

4. The process of claim 1 wherein said aromatic radical is phenyl or naphthyl.

5. The process of claim 1 wherein said aromatic radical carries at least one substituent other than sulfonate and/or carboxylate.

6. The process of claim 5 wherein said said substituent is fluorine.

7. The process of claim 1 wherein said anion is selected from the group consisting of triphenylphosphine mono-, di-, or trisulfonates or -carboxylates.

8. The process of claim 1 wherein said anions are biaryl compounds, substituted by at least one sulfonate or carboxylate of the formula

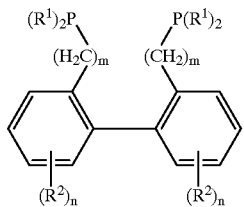

wherein
  $R^1$'s are individually alkyl, cycloalkyl, phenyl, tolyl, or naphthyl;
  $R^2$'s are individually hydrogen, alkyl having 1 to 14 carbon atoms, alkoxy having 1 to 14 carbon atoms, or are cycloalkyl, aryl, or aryloxy, each having 6 to 14 carbon atoms, or is a fused-on benzene ring;
  the m's are individually integers from 0 to 5, and the n's are individually integers from 0 to 4.

9. The process of claim 8 wherein said anion is the product of sulfonation of 2,2'-bis(diphenylphosphinomethyl)-1,1'-biphenyl or 2,2'-bis(diphenylphosphinomethyl)-1,1'-binaphthyl.

10. The process of claim 1 wherein said anion is 3,4-dimethyl-2,5,6-tris(p-sulfonatophenyl)-1-phosphanorbornadiene.

11. The process of claim 1 wherein said cation is trimethylcetylammonium, trimethyldodecylammonium, tributyldodecylammonium, dodecylethyldimethylammonium, triethylbenzylammonium, trimethyltetradecylphosphonium or tributylhexadecylphosphonium.

* * * * *